United States Patent
Parkins

(10) Patent No.: US 6,665,410 B1
(45) Date of Patent: Dec. 16, 2003

(54) ADAPTIVE FEEDBACK CONTROLLER WITH OPEN-LOOP TRANSFER FUNCTION REFERENCE SUITED FOR APPLICATIONS SUCH AS ACTIVE NOISE CONTROL

(76) Inventor: John Warren Parkins, 235 S. Buckhout St., #B7, State College, PA (US) 16801

( * ) Notice: Subject to any disclaimer, the term of this patent is extended or adjusted under 35 U.S.C. 154(b) by 0 days.

(21) Appl. No.: 09/076,553

(22) Filed: May 12, 1998

(51) Int. Cl.$^7$ ................................................ A61F 11/06
(52) U.S. Cl. .................... 381/71.1; 381/71.11; 381/71.8
(58) Field of Search ............................ 381/71.1–71.14, 381/73.1, 94.1–94.9, 96, 83.93, 95; 708/322, 280

(56) References Cited

U.S. PATENT DOCUMENTS

| | | |
|---|---|---|
| 4,455,675 A | 6/1984 | Bose |
| 4,489,441 A | 12/1984 | Chaplin |
| 4,527,282 A | 7/1985 | Chaplin |
| 4,769,766 A | 9/1988 | Tung |
| 4,987,598 A | 1/1991 | Eriksson |
| 5,159,547 A | 10/1992 | Chand |
| 5,182,774 A | 1/1993 | Bourk |
| 5,229,699 A | 7/1993 | Chu |
| 5,386,477 A | 1/1995 | Popovich |
| 5,600,729 A | 2/1997 | Darlington |

OTHER PUBLICATIONS

Bernard Widrow & Samuel D. Stearns Adaptive Signal Processing, 1985, pp. 99–103 Simon & Schuster Company, Upper Saddle River, NJ.
Sen M. Kuo & Dennis R. Morgan Active Noise Control Systems—Algorithms and DSP Implementations 1996, pp. 58–65, 90–95, Wiley & Sons, Inc., NY, NY.

Primary Examiner—Duc Nguyen
Assistant Examiner—Lun-See Lao

(57) ABSTRACT

An adaptive feedback control system (7) has a feedback loop (8) and a digital adaptive compensation filter (10). An auxiliary noise signal (30) is added to a reference signal (26) for use in residual-loop gain identification. A residual-loop gain identifier uses the noise signal (30) and a signal taken from the output of the compensation filter (29) to determine the residual-loop gain transfer function of the system. Once the residual-loop gain has been determined, the filter coefficients from the identifier are copied to an open-loop gain adaptor (18). The actual open-loop gain transfer function of the system is compared to a reference open-loop gain transfer function. The compensation filter (10) is adapted so that the desired open-loop gain transfer function for the system is achieved.

11 Claims, 4 Drawing Sheets

ADAPTIVE FEEDBACK CONTROLLER WITH OPEN-LOOP TRANSFER FUNCTION REFERENCE SUITED FOR APPLICATIONS SUCH AS ACTIVE NOISE CONTROL

BACKGROUND-FIELD OF INVENTION

This invention relates to feedback control systems, specifically to systems which are automatically adjusted to match performance criteria. This invention is suited for use in various applications, such as acoustic active noise control systems.

BACKGROUND-DESCRIPTION OF PRIOR ART

Feedback is often used to improve the performance of a system to be controlled (also known as a plant). Feedback improves the performance of an open-loop system by reducing the effects of disturbance noises and by reducing the sensitivity of the system to changes in the open-loop transfer function response. Thus, the output of the plant is able to track the input reference signal more accurately. Feedback control systems, also known as closed-loop control systems, are ubiquitous in modern day technology. Some applications include: automobile cruise control, missile guidance, chemical process control, robotic control, and active noise control. In active noise control devices, undesirable acoustic noise at the system output is reduced by producing a signal, through feedback, to destructively interfere with the noise.

The performance of a feedback system is determined by its open-loop transfer function, which includes the plant. The spectra of the noise attenuated by a stable feedback system is related to the frequency region were the magnitude of the open-loop transfer function is greater than unity (often called the control bandwidth). As the frequency span of the control bandwidth increases the frequency span of noise reduction increases until instability is approached. As the amplitude of the open-loop transfer function is increased, in the control bandwidth, the performance of noise attenuation increases until instability is approached. Although feedback control systems exhibit a reduced sensitivity to changes in the plant, compared to open-loop systems, the performance of a feedback system will change as the plant characteristics change. Therefore, the basic feedback system will suffer performance degradation if the plant is not stable.

Unfortunately, some plants have widely varying characteristics. An example of this is an active control headset disclosed in U.S. Pat. No. 5,182,774. This type of noise-attenuating headset employs a basic feedback system with a microphone and a speaker. The sensitivity of the microphone and speaker may change significantly as temperature and humidity conditions change. Also, the acoustic response of the earcup cavity in the headphones varies due to acoustic leaks around the earcusion and differences in ear geometries. In order to avoid instability, the open-loop gain and control bandwidth are reduced to account for these changes in the plant. This results in sacrificed performance.

Some feedback controllers, often called "self-tuning", measure parameters of the closed-loop system during operation, and use this information to modify these parameters in a compensation filter. These systems are typically used in proportional integral differential (PID) controllers as seen in U.S. Pat. No. 5,159,547. The proportional, integral, and derivative gain constants are measured in the closed-loop system, and these parameters are then updated. But many controllers, such as those used for active noise control systems, use a more sophisticated compensation filter which uses many more than three parameters to define the filter as in U.S. Pat. No. 4,455,675. These more sophisticated compensation filters have many poles and zeros, and are defined by a transfer function curve. It would be very difficult to use a self-tuning controller in this case, because of the complex transfer function.

Another related technology uses an open-loop system and a model reference as seen in U.S. Pat. No. 5,386,477. This system uses a digital filter as a model reference, and adapts filters so that the overall feedforward response matches that of the model reference. Feedforward controllers do not perform as well as feedback controllers for many applications, especially when attenuating non-repetitive noise at the output. The feedforward model reference system will not work in a feedback system.

The inventor has discovered that a feedback system that maintains a constant open-loop transfer function, even when the plant or other components within the feedback loop change with time, would allow one to maximize the performance of the overall system.

SUMMARY OF THE INVENTION

The invention described herein is a simple solution to problems stated above. Without breaking the control loop, an embodiment of the invention measures the residual-loop transfer function during operation, and compares the estimated open-loop transfer function to a reference open-loop transfer function. The reference open-loop transfer function is determined by the designer to yield optimal performance of a given plant. A digital compensation filter in the controller adapts so that the actual open-loop transfer function sufficiently matches the reference. This results in a simple and inexpensive yet robust feedback controller that maintains a relatively constant open-loop transfer function even when components of the feedback system change over time. In this way the performance of the plant is optimized.

DRAWING FIGURES

In the drawings, closely related figures have the same number but different alphabetic suffixes.

DETAILED DESCRIPTION OF THE DRAWINGS

Figure 1A:
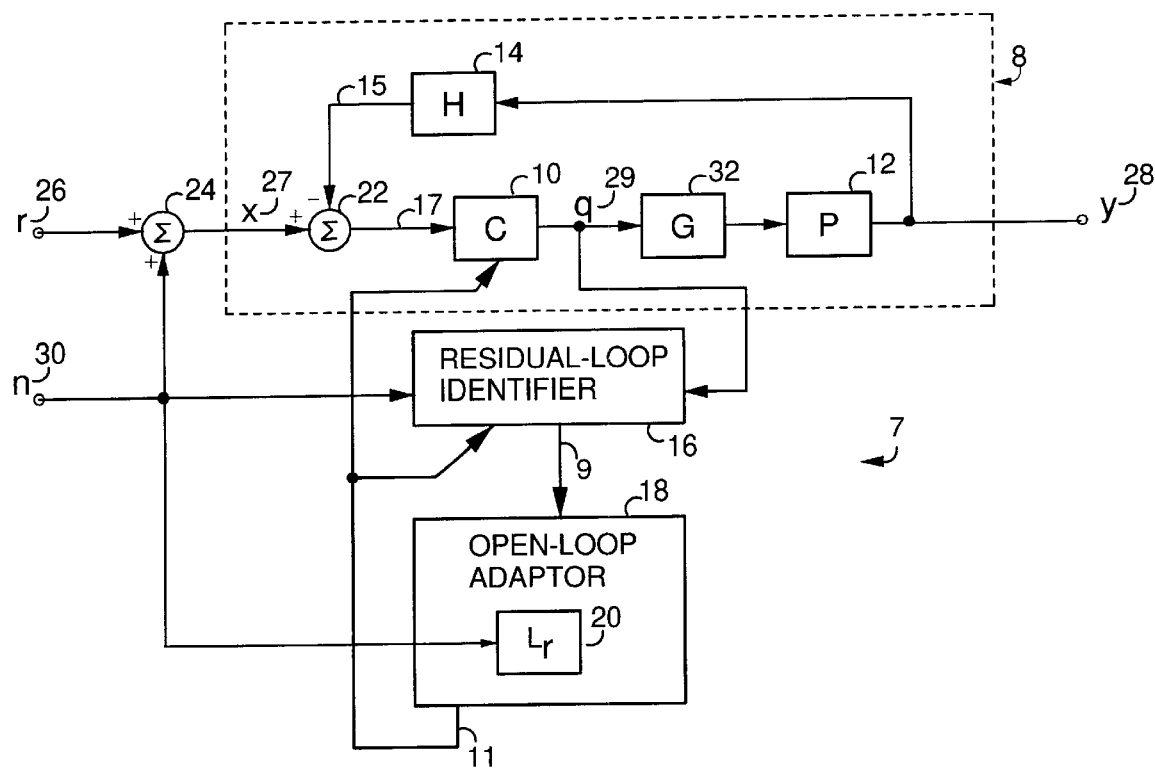
FIG. 1A is a schematic illustration of an adaptive feedback controller with open-loop transfer function reference.

FIG. 1A shows one preferred embodiment of the adaptive feedback controller with open-loop transfer function reference at 7. A feedback controller at 8, is similar to a conventional feedback controller of the prior art. A signal x at 27 is used to control a plant at 12 represented by the transfer function P. An output of the plant y at 28 is filtered by a general feedback transfer function H at 14, which represents the total transfer function of the feedback path. A filtered feedback signal at 15 is subtracted from x at a summer at 22. A resulting error signal at 17 is filtered by a digital adaptive compensation filter with transfer function C at 10, which is designed to achieve a desired open-loop response when cascaded with an auxiliary gain filter G at 32, the plant transfer function P and the feedback transfer function H. The open-loop transfer function is specified by a designer to achieve optimal performance of the plant in question. A filtered error signal q at 29 is then input to the auxiliary gain filter G, which comprises a conventional power amplifier and/or any known electronic filtering. If the output y of the plant is greater than that defined by x, the signal at 15 subtracts from x, lowering the output y. In this way, the feedback controller 8 can control the output y of the plant accurately.

The embodiments of the invention described below use digital filters to significantly improve the performance of the feedback controller 8. The digital filters used in this and later embodiments are preferably finite impulse response (FIR) filters, though many other types of filters may be used to achieve similar results, such as infinite impulse response (IIR) filters, correlation filters, and frequency domain filters. The output of an FIR filter is defined by the following equation, $$y(n+1)=W(n)X(n) \quad \text{(equation 1)}$$

where $y(n+1)$ is the new filter output value. $W(n)$ is a row vector of length N containing the current values of the N filter coefficients, and $X(n)$ is a column vector containing the current value of the input and the N−1 previous values of the input. n is an integer.

Under the preferred embodiment, the feedback controller 8 is significantly improved though the use of the following additional components and systems. A reference signal r at 26 controls the plant 12. The reference signal may be a communication signal, a position signal, or any control signal desired to appear at the output of the plant 12. A broadband auxiliary noise signal n at 30 is added to the reference signal r with a summer at 24. The auxiliary noise n is used to generate a broadband excitation of the feedback controller 8, and can be produced by a conventional random noise source (not shown). The auxiliary noise n is input to a residual-loop identifier at 16 along with the filtered error signal q. The residual-loop identifier 16 is a digital system which provides a means for estimating the residual-loop gain transfer function of the feedback controller 8. The residual-loop transfer function estimate is in the form of filter coefficient values for a digital filter. The auxiliary noise n is low enough in amplitude so as not to cause the output y from deviating substantially from the desired output. The open-loop transfer function of the basic feedback controller 8, is the transfer function of the forward path in the loop, in series with the feedback path, and is $$L=CGPH \quad \text{(equation 2)}$$

while the residual-loop transfer function is defined as $$R = \frac{L}{C} = GPH \quad \text{(equation 3)}$$

Once the identifier 16 has estimated the residual-loop transfer function, filter coefficients of the residual-loop estimate at 9 are copied to an open-loop adaptor at 18. The open-loop adaptor 18 is a digital system which provides a means for determining the optimal filter coefficients for the adaptive compensation filter C. The open-loop gain adaptor 18 receives the auxiliary noise n, the residual open-loop estimate filter coefficients, and uses an open-loop gain reference transfer function $L_r$ at 20 along with the current filter coefficients of the adaptive compensation filter to form new adaptive compensation filter coefficients which in series with the residual-loop transfer function yield approximately the same open-loop transfer function as the reference open-loop transfer function. The open-loop reference transfer function $L_r$, is the desired open-loop response of the controller 8. The open-loop reference transfer function $L_r$, is in the form of filter coefficient values for a digital filter.

Upon convergence of the adaptor 18, updated coefficients for the adaptive compensation filter at 11 are copied to the feedback controller 8 and the identifier 16. This process is repeated continuously. In this way the open-loop transfer function of the feedback controller 8 remains constant even if the plant P, auxiliary gain G, or feedback H transfer functions change over time. For example, if the overall gain of the feedback H increases over time, the overall gain of the adaptive compensation filter C will decrease proportionally. Residual-loop identifiers and an open-loop adaptor are disclosed in further embodiments of the invention.

Figure 1B:
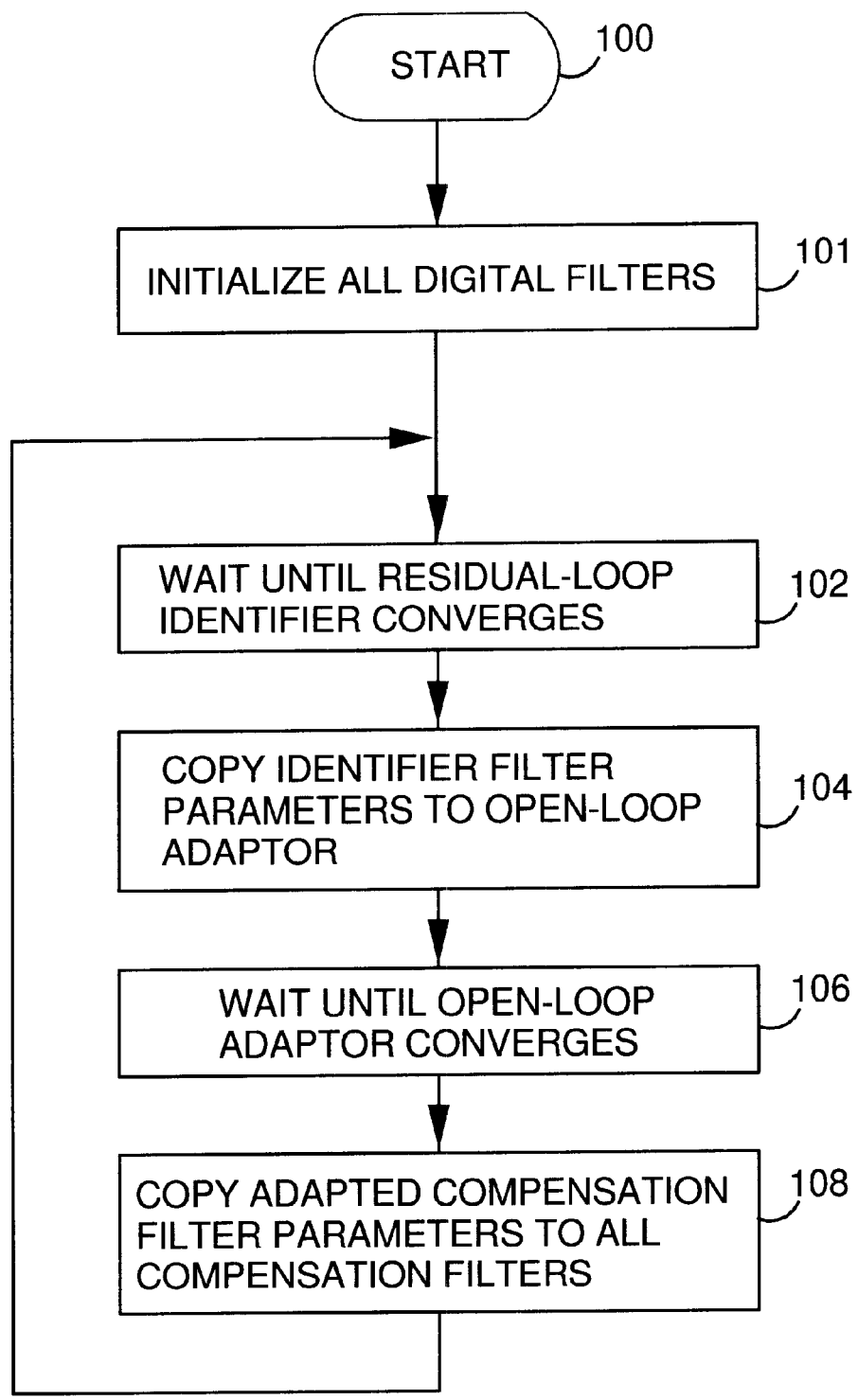
FIG. 1B is a flow chart of a processing algorithm of the invention.

FIG. 1B shows a flow chart of the process involved in FIG. 1A. All digital filters in the identifier 16, adaptor 18 and the adaptive compensation filter 10 are first initialized to coefficients at 101 producing the desired open-loop response under typical plant conditions. These initial values are predetermined based on empirical data. The system waits at 102 until the residual-loop identifier 16 has sufficiently converged to an estimate of the actual residual-loop transfer function. This may be accomplished by the use of a timer, or an algorithm which monitors the incremental changes made to the estimate of the residual-loop. When the changes are sufficiently small (below a predetermined threshold), the identifier 16 has converged. The estimate of the residual-loop 9 is copied to the open-loop adaptor at 104. Another timer, or algorithm may be used to wait a sufficient time for the open-loop adaptor to converge at 106. Next, the adaptive compensation filter coefficients 11 are copied to all instances of the compensation filter in the system at 108. Steps 102–108 are repeated during the operation of the adaptive feedback controller with open-loop reference transfer function 7 of FIG. 1A.

Figure 2:
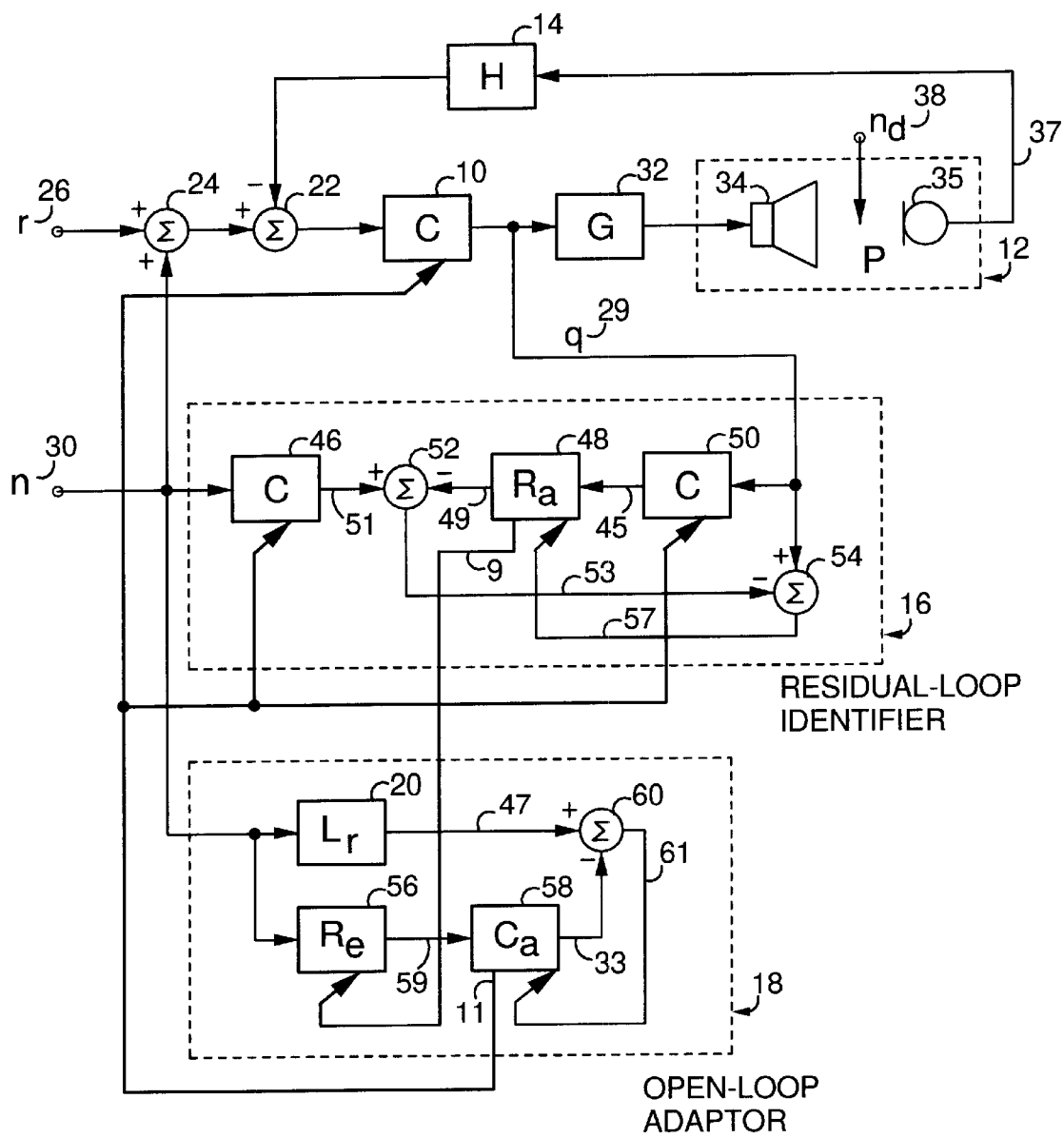
FIG. 2 is like FIG. 1A and shows a further embodiment.

FIG. 2 is like FIG. 1A, and shows another embodiment of FIG. 1A when the system is used for active noise control in a headset or earplug. The plant 12 in this embodiment consists of a speaker at 34 and a microphone at 35 along with the acoustic response of a cavity incorporating the speaker and microphone. The speaker with microphone and acoustic cavity have a total transfer function P. The plant response may significantly change with temperature and humidity. It is desired to drive the speaker so as to reduce, as much as possible, an output of the microphone at 37, due to an acoustic noise disturbance $n_d$ at 38, while providing appropriate gain for the reference signal r 26. The reference signal r is often a communication signal. The adaptive compensation filter C 10 is a digital FIR filter, but other digital filter forms may be used with similar results.

The auxiliary noise source n 30 provides the broadband signal necessary for the identification of the residual-loop transfer function. A digital filter C at 46 has the same filter coefficients as the adaptive compensation filter 10. A digital filter C at 50 also has the same filter coefficients as the filter at 10. The noise signal n is filtered by the filter C 46, resulting in a filter output 51. The signal q at 29, taken from the output of the adaptive compensation filter 10, is filtered by filter C 50 to produce a signal at 45 which is then filtered by an adaptive filter $R_a$ at 48, to yield a filter output 49. The signal 49 is subtracted from the signal 51 to yield an error signal at 53. This error signal 53 is subtracted from the adaptive compensation filter output signal q by the use of a summer at 54. A resulting error signal at 57 and the signal 45 are then used to update the adaptive filter $R_a$ using a well-known least mean squares (LMS) algorithm, though other adaptive algorithms may be used. The coefficients of filter $R_a$ are adapted using the following formula, $$W(n+1)=W(n)+\mu X(n)e(n) \quad \text{(equation 4)}$$

where W(n+1) is a row vector of length N containing the new filter coefficients of $R_a$. W(n) is a row vector of length N containing the current filter coefficients, and X(n) is a row vector of length N containing the current and previous N−1 samples from signal 45. e(n) is the current value of signal 57, and $\mu$ is a convergence constant chosen by the designer to ensure stability of the adaptive process. n is an integer. As the residual-loop identifier converges, the error signal at 57 is reduced to the point where changes in W(n+1) are minimal. Upon convergence of the adaption process, $R_a$ will be an accurate estimate of the residual-loop transfer function.

Once the residual-loop gain transfer function has been estimated, the filter coefficients of $R_a$ 9 are copied to a filter $R_e$ at 56. $R_e$ is the estimated residual-loop transfer function. The random noise signal n 30 is input to $R_e$ and the open-loop transfer function reference $L_r$. A filter output signal at 59 is the input to an adaptive filter $C_a$ at 58. An output of this adaptive filter at 33 is subtracted from an output of $L_r$ at 47 to yield error signal 61. The error signal 61 along with the signal 59 are used to update the adaptive filter $C_a$ using an LMS algorithm, though other adaptive algorithms may be used with similar results. Here again, equation 4 is used to update the filter coefficients of Ca. In this case W(n+1) is a row vector of length M containing the new filter coefficients of $C_a$. W(n) is a row vector of length M containing the current filter coefficients, and X(n) is a row vector of length M containing the current and previous M−1 samples from signal 59. e(n) is the current value of signal 61, and $\mu$ is a convergence constant chosen by the designer to ensure stability of the adaptive process. n is an integer. When the error signal at 61 is sufficiently small (below a threshold level determined by the designer), the adaptive filter $C_a$ has converged to a transfer function that will yield the desired open-loop response. Filter coefficients of $C_a$ at 11 are then copied to the adaptive compensation filter 10, and the other instances of filter C located at 46 and 50. The process is continuously repeated. In this way the open-loop transfer function of the feedback system remains constant even if the plant P, auxiliary gain G, or feedback H transfer functions change over time.

Figure 3:
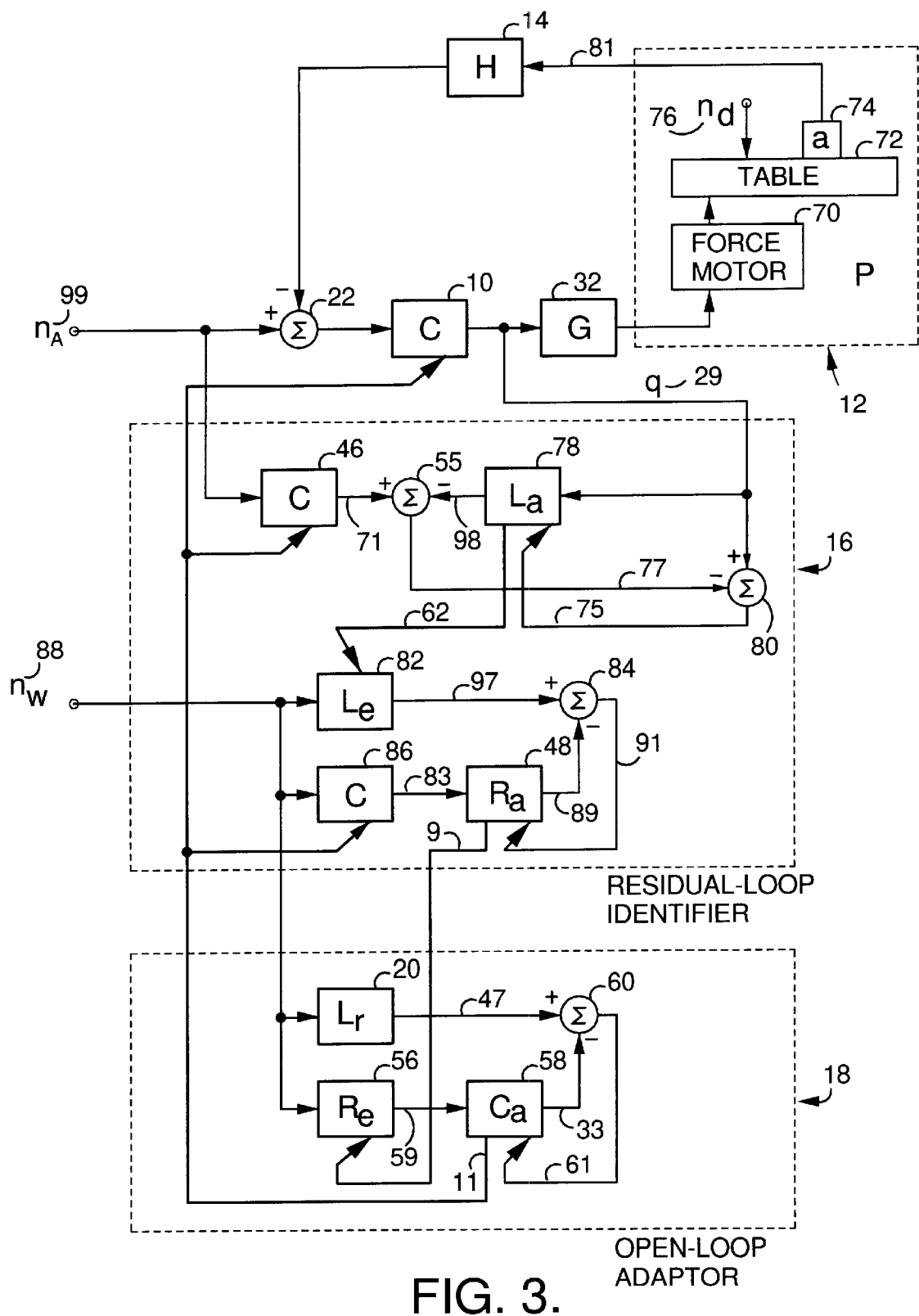
FIG. 3 is like FIG. 1A and shows a further embodiment.

FIG. 3 is like FIG. 1A, and shows another embodiment of FIG. 1A when the system is used for active vibration control of a table. FIG. 3 uses similar notation and reference numerals as FIGS. 1A and 2 where appropriate to facilitate understanding. The plant 12, this time comprises a force motor at 70, a table at 72 and an accelerometer at 74. A vibration noise disturbance $n_d$ at 76 acts on the table. It is desired that the table not vibrate due to the noise disturbance. The accelerometer provides a sensing signal at 81 for the controller, and ultimately a control signal is derived from the accelerometer output and input to the force motor which counteracts the disturbance. Thus the table becomes substantially unaffected by external vibration disturbances. This embodiment also has the residual-loop identifier 16 and the open-loop adaptor 18. With the addition of these two systems and auxiliary noise sources, the adaptive compensation filter 10 is updated, on line, so that the open-loop transfer function remains constant and equal to the open-loop transfer function reference 20 even if G, P and H vary with time. In this embodiment the open-loop adaptor functions in the same way as that in FIG. 2.

In this embodiment, an auxiliary noise source $n_A$ at 99 is input to the system without the addition of a reference signal. The noise signal 99 is input to the filter C 46 and produces an output 71. A second auxiliary noise signal $n_w$ at 88 is used in this embodiment for adaption. The second noise source may have different characteristics than the first to improve performance of system identification. For example, the second noise source may have a higher amplitude than the first. Since the second noise source is not added to the feedback system, this noise source with increased amplitude will not appear at the plant output 81.

The residual-loop identifier 16 in this embodiment uses a two-step process instead of the single-step process shown in FIG. 2. The compensation filter output q is input to an adaptive filter $L_a$ at 78. An output of this filter at 98 is subtracted from the signal 71 using a summer at 55; an error signal at 77 results. This error signal 77 is subtracted from the signal q, with a summer at 80 to yield another error signal at 75. The error signal at 75 along with the signal q are used to adapt filter $L_a$ using the LMS adaption method disclosed earlier, or any other adaption algorithm yielding similar results. The filter $L_a$ converges to an estimate of the open-loop transfer function of the system. In this way the open-loop gain of the system has been identified. After convergence, filter coefficients of $L_a$ at 62 are copied to a filter $L_e$ at 82. $L_e$ is an estimation of the open-loop transfer function. Noise source $n_w$ is input to $L_e$ and to a filter C at 86. An output signal at 83 of the filter is then filtered by the adaptive filter $R_a$ at 48. An output signal at 89 of filter $R_a$ is subtracted from an output signal at 97 of filter $L_e$ using a summer at 84. A resulting error signal at 91, along with the signal 83 are used to adapt the filter $R_a$, using the LMS algorithm disclosed earlier, or any adaptive algorithm that would yield similar results. Upon convergence, filter coefficients of $R_a$ at 9 are copied to the filter $R_e$ 56. $R_e$ will be an estimate of the residual-loop transfer function of the feedback system. As in FIG. 2, $C_a$ 58 converges to a filter transfer function that will yield the desired open-loop transfer function when cascaded with the residual-loop transfer function. The filter coefficients of $C_a$ 11 are then copied to the adaptive compensation filter at 10, and the other instances of filter C located at 46 and 86.

The embodiment in FIG. 3 requires more time for system identification and adaption, but produces better estimates for the residual-loop transfer function, and adaptive compensation filter C. This system will produce vibrations due to noise source $n_A$, but will perform very well when the noise disturbance $n_d$ is large enough to make the noise vibration due to $n_A$ tolerable.

Although specific embodiments of, and examples for, the present invention are described herein for illustrative purposes, various equivalent modifications are possible within the scope of the invention, as will be recognized by those skilled in the relevant art. The teachings provided herein of the present invention can be applied to other feedback control systems, not necessarily the exemplary active noise control and active vibration control systems described above. Various exemplary digital filters types and signal processing procedures under the present invention can be employed.

These and other changes can be made to the invention in light of the above detailed description. In general, in the following claims, the terms used should not be construed to limit the invention to the specific embodiments disclosed in the specification and the claims, but should be construed to include all feedback control systems that operate under the claims to provide a method for maintaining a constant open-loop transfer function even when the transfer functions of components within the control loop change. Accordingly, the invention is not limited by the disclosure, but instead its scope is to be determined entirely by the following claims.

I claim:

1. An adaptive feedback controller comprising:
a feedback control loop comprising an adaptive filter, wherein the feedback control loop has a residual-loop gain transfer function;
an estimating circuit coupled to the feedback control loop that estimates the residual-loop gain transfer function;
and a comparing circuit coupled to the feedback control loop to compare the estimated residual-loop gain transfer function with a predetermined reference open-loop gain transfer function to produce a comparison signal, wherein the adaptive filter receives the comparison signal and modifies the open-loop gain transfer function of the feedback control loop to approximately match the reference open-loop gain transfer function.

2. The invention according to claim 1 further comprising: a summer receiving an auxiliary noise source and summing an auxiliary noise signal to the estimating and comparing circuits.

3. The invention according to claim 1 wherein the estimating circuit includes a filter having a transfer function similar to a transfer function of the adaptive filter, and wherein the filter of the estimating circuit filters noise to estimate at least a portion of the residual-loop gain transfer function.

4. The invention according to claim 1 wherein the estimating circuit includes a filter to filter an output of the adaptive filter and produce an estimate of at least a portion of the residual-loop gain transfer function.

5. The invention according to claim 1 wherein the estimating and comparing circuits include least mean square circuits for estimating at least a portion of the residual-loop gain transfer function.

6. The invention according to claim 1, wherein the residual-loop gain transfer function comprises a quotient, the quotient having as a numerator thereof an open-loop gain transfer function and having as a denominator thereof a transfer function of the adaptive filter.

7. A method of feedback control comprising the steps of:
estimating a residual-loop gain transfer function of a feedback control loop;
comparing the estimate of the residual-loop gain transfer function with a predetermined reference open-loop gain transfer function of the feedback control loop;
and matching the open-loop gain transfer function of the feedback control loop with the reference open-loop gain transfer function.

8. The method according to claim 7 further comprising: summing an auxiliary noise signal to the residual-loop gain transfer function.

9. The method according to claim 7 wherein estimating a residual-loop gain transfer function includes determining least mean squares estimates of the residual-loop gain.

10. The invention according to claim 7, wherein the step of estimating a residual-loop gain transfer function of a feedback control loop comprises estimating a residual-loop gain transfer function of a feedback control loop comprising an adaptive filter, wherein the residual-loop gain transfer function comprises a quotient, the quotient having as a numerator thereof an open-loop gain transfer function and having as a denominator thereof a transfer function of the adaptive filter.

11. An adaptive feedback controller comprising:
a feedback control loop comprising an adaptive filter, said feedback control loop generating a filtered error signal;
a residual loop identifier coupled to said feedback control loop to receive therefrom said filtered error signal, said residual loop identifier configured to generate a parameter of an estimated residual loop transfer function in response to said filtered error signal; and
an open loop adaptor coupled to said residual loop identifier and to said adaptive filter, said open loop adaptor configured to receive from said residual loop identifier said parameter of said estimated residual loop transfer function and to form a new adaptive filter coefficient, said open loop adaptor configured to copy said new adaptive filter coefficient to said adaptive filter, so as to adjust a behavior of said feedback control loop.

* * * * *